United States Patent [19]

Germany et al.

[11] Patent Number: 5,329,804
[45] Date of Patent: Jul. 19, 1994

[54] CALIBRATION SYSTEM AND METHOD FOR CALIBRATING A BLOOD GAS SENSOR

[75] Inventors: Cheryl D. Germany, Kirkland; Conrad T. Oi Fong, Redmond; Steven B. Duke, Bothell, all of Wash.; Gerald G. Vurek, Mountain View, Calif.

[73] Assignee: Abbott Laboratories, Abbott Park, Ill.

[21] Appl. No.: 962,990

[22] Filed: Oct. 16, 1992

[51] Int. Cl.$^5$ ............................................. G01N 33/00
[52] U.S. Cl. ...................................................... 73/1 G
[58] Field of Search ................. 73/1 G, 1 R; 128/637; 436/11; 364/571.01–571.03; 219/10.67, 201, 221, 385, 386, 490, 521, 524; 236/20 R

[56] References Cited

U.S. PATENT DOCUMENTS

| | | | |
|---|---|---|---|
| 4,361,539 | 11/1982 | Weinberg et al. | 422/68 |
| 4,498,496 | 2/1985 | Bascellona et al. | 73/1 G |
| 4,531,398 | 7/1985 | Di Benedetto et al. | 73/1 G |
| 4,597,285 | 7/1986 | Kuchar et al. | 73/1 G |
| 4,600,697 | 7/1986 | Smernoff | 436/11 |
| 4,691,557 | 9/1987 | Dunn et al. | 73/32 A |
| 4,863,016 | 9/1989 | Fong et al. | 206/210 |
| 4,941,308 | 7/1990 | Grabenkort et al. | 53/425 |
| 5,061,631 | 10/1991 | Calabrese | 436/11 |
| 5,111,836 | 5/1992 | Grabenkort | 137/68.1 |
| 5,157,957 | 10/1992 | Mettes et al. | 73/1 G |
| 5,207,087 | 5/1993 | Costello | 73/1 G |

FOREIGN PATENT DOCUMENTS

0470818A2 12/1992 European Pat. Off. .
0128840 8/1982 Japan .................................. 73/1 G

Primary Examiner—Robert Raevis
Attorney, Agent, or Firm—Christensen, O'Connor, Johnson & Kindness

[57] ABSTRACT

A calibration system and method for calibrating a medical sensor (16) that monitors chemical blood gases. A calibrator (12) is used in connection with a tray (14) in which the medical sensor is stored in a sterile environment, both before and during the calibration process. The medical sensor is immersed in a liquid (30) in a tonometry chamber (28) defined in the tray and covered by a membrane (120/122) that is permeable to gas, but impermeable to bacteria. During the calibration process, the tray is inserted into the calibrator, bringing a heated platen (26) into contact with the tonometry chamber, so that the liquid can be heated to a calibration temperature substantially equal to the temperature at which the medical sensor will subsequently be used. A first calibration gas is then bubbled through the liquid until a saturated condition is achieved. Once the temperature of the liquid is increased to the desired calibration temperature, as determined by a temperature sensor on the medical sensor, data for a first calibration point is taken. A second calibration gas is then bubbled through the liquid until saturation is achieved, yielding data for a second calibration point, for each of the chemical blood gas parameters. The calibration data is processed to determine calibration coefficients that will be applied to the medical sensor.

17 Claims, 10 Drawing Sheets

CALIBRATION SYSTEM AND METHOD FOR CALIBRATING A BLOOD GAS SENSOR

FIELD OF THE INVENTION

The present invention is a calibration system and a method for calibrating a medical sensor, and more specifically, is used to calibrate a chemical blood gas sensor at a plurality of calibration points.

BACKGROUND OF THE INVENTION

A chemical blood gas sensor (a preferred embodiment being referred to as a HEMOMETRIX TM sensor) has been developed for monitoring $pCO_2$, $pO_2$, and pH in a patient's vascular system. The sensor is disposed at the distal end of an optical fiber and is introduced into a patient's blood stream through a preinserted catheter. To facilitate ease of use and handling of the HEMOMETRIX TM sensor, it is packaged in a sterile environment during storage and shipment from the manufacturer to the point of use. This sterile environment comprises a flat tray having a plurality of compartments that hold various components of the sensor and of a delivery device that is connected to the catheter for introduction of the sensor into the patient's bloodstream. The tray is covered with a gas permeable sheet of TYVEK TM that resists penetration by bacteria, but allows sterilization of the package and its contents by exposure to ethylene oxide (ETO) gas. U.S. Pat. Nos. 4,863,016 and 5,111,836, owned by the same assignee as the present case, disclose details of the packaging and other related aspects. The disclosure and drawings of U.S. Pat. Nos. 4,863,016 and 5,111,836 are hereby specifically incorporated herein by reference, since many of the components and configuration of the package for the sensor that are disclosed therein directly relate to the present invention.

At the time that the HEMOMETRIX TM sensor is packaged, a tonometry chamber in which the sensor is disposed is filled with a buffered hydration solution from a pouch connected to the chamber by plastic tubing, immersing the sensor in the hydration solution. After the tonometry chamber is filled, a "guillotine" valve provided in the tray is actuated, severing and sealing the line, so that the pouch can be discarded. The tray is then sealed in a gas impermeable wrap and remains sealed until the HEMOMETRIX TM sensor is to be calibrated, just prior to the sensor's use.

Since it is important to maintain the HEMOMETRIX TM sensor and its associated apparatus in a sterile environment, a calibration method and apparatus for calibrating the sensor while it is in the tray and covered by the gas permeable sheet are required. Furthermore, although it is possible to calibrate the sensor at ambient temperature and then apply temperature corrections to the readings of blood gas values obtained with the sensor at the substantially higher temperature of its use in vivo, the results are not entirely satisfactory. Much more accurate measurements can be obtained with the HEMOMETRIX TM sensor by calibrating at a plurality of calibration points made at a calibration temperature that is substantially equal to the temperature at which the sensor will actually be used, i.e., at the temperature of the patient's blood, 37° C. Before the sensor is calibrated, it must be immersed in a calibration solution to obtain a first calibration point. Ideally, the calibration solution should then be chemically modified to obtain a second calibration point, to improve the accuracy with which it subsequently monitors the blood gases and pH. No prior art calibration device or method provides the facility to calibrate an in vivo blood gas sensor at the temperature it will be used in the patient and at a plurality of calibration points, while maintaining the sensor in its sterile environment.

SUMMARY OF THE INVENTION

In accordance with the present invention, a calibration system is defined for calibrating a medical sensor sensitive to a chemical parameter, the medical sensor being disposed in a liquid pool contained within a housing that maintains the medical sensor in a sterile environment during calibration of the medical sensor, prior to its in vivo use. The calibration system comprises a chassis adapted for supporting the housing in which the medical sensor is disposed, and a heater disposed on the chassis for heating a liquid in a portion of the housing in which the medical sensor is held, to a predefined calibration temperature. A source of a first calibration gas is connected in fluid communication with a port, the port being adapted to connect to a fluid line, which extends from the housing, to enable the first calibration gas to bubble through the liquid in which the medical sensor is disposed. Valve means, connected in fluid communication with and between the source of the first calibration gas and the port, are opened to enable a flow of the first calibration gas through the port during the calibration of the medical sensor. As the first calibration gas bubbles through the liquid, a first predefined chemical calibration point is achieved. Biasing means, disposed on the chassis, bias the heater against the housing to ensure heat transfer from the heater to the liquid in which the medical sensor is disposed.

Temperature control means, electrically coupled to the heater, are adapted to connect to a lead coupled to the medical sensor. This lead conveys a signal produced by the medical sensor, which is indicative of the temperature of the liquid; the temperature control means control the temperature of the heater so that the liquid in which the medical sensor is disposed is heated to the predefined calibration temperature and maintained at that temperature during the calibration of the medical sensor.

A method for calibrating the medical sensor and a method for heating a liquid to a predefined calibration temperature in order to calibrate an intravascular medical sensor are further aspects of this invention. The method of calibrating includes steps that are generally consistent with the functions performed by the elements of the calibration system discussed above.

The method for heating the liquid includes the steps of providing a first predefined level of power to heat the liquid, and extrapolating a current temperature of the liquid to determine an extrapolated temperature after a first predefined time interval. A second predefined level of power is then provided to heat the liquid when the extrapolated liquid temperature is at least equal to the calibration temperature, the second predefined level of power being less than the first predefined level of power. After the temperature of the liquid begins to decrease, the calibration temperature is adjusted as a function of the current temperature of the liquid. A third predefined level of power is applied to heat the liquid in an attempt to maintain the liquid at the calibration temperature until the calibration is complete—but only if the extrapolated temperature is less than the calibration temperature. If not, the second predefined level of power is provided to heat the liquid. This method rapidly raises the temperature of the liquid to the desired calibration temperature and maintains that temperature substantially constant during the calibration process.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
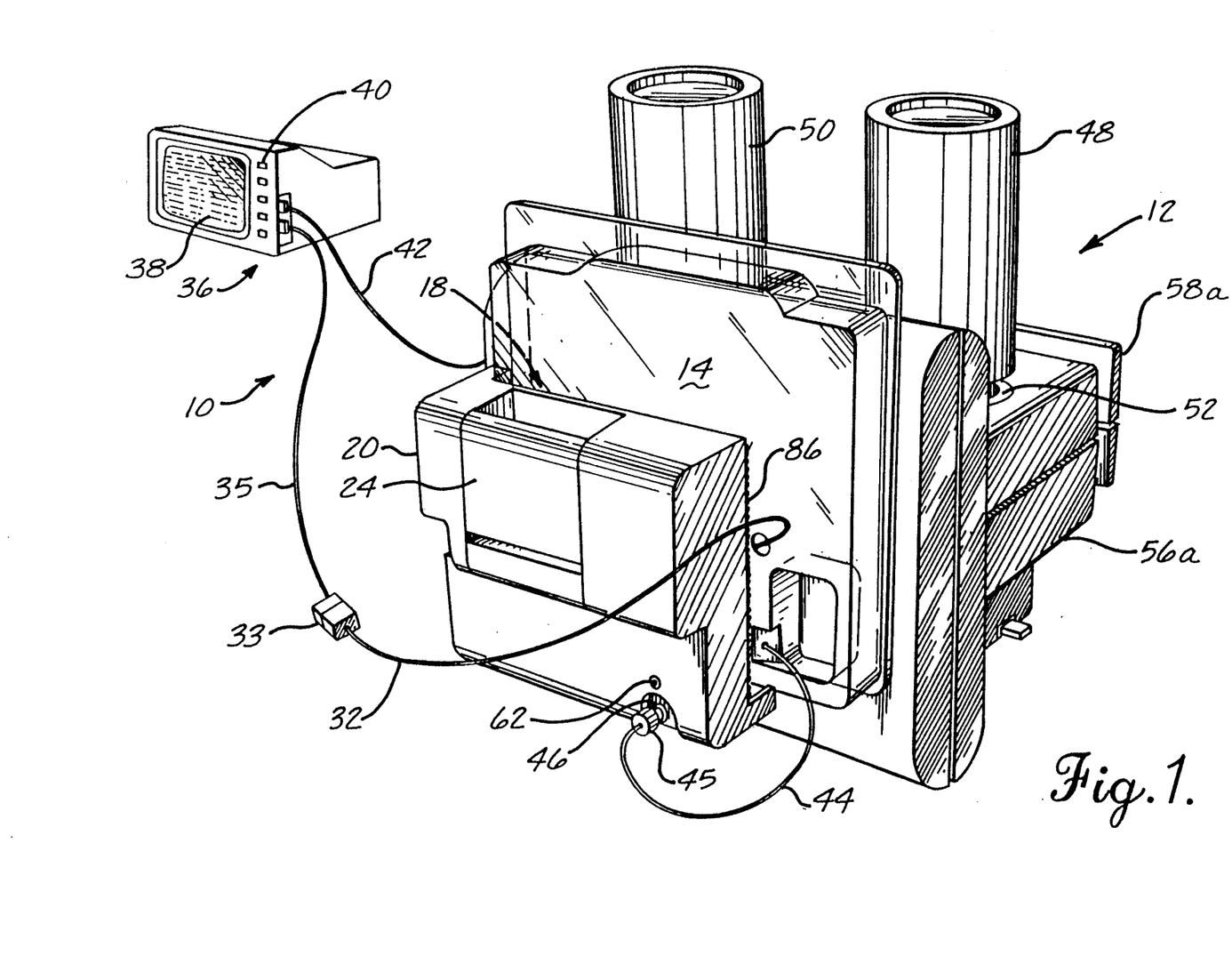
FIG. 1 is a perspective view of a calibrator and display unit in accordance with the present invention, showing a tray containing a medical sensor to be calibrated, positioned as required for calibration of the medical sensor.
Figure 2:
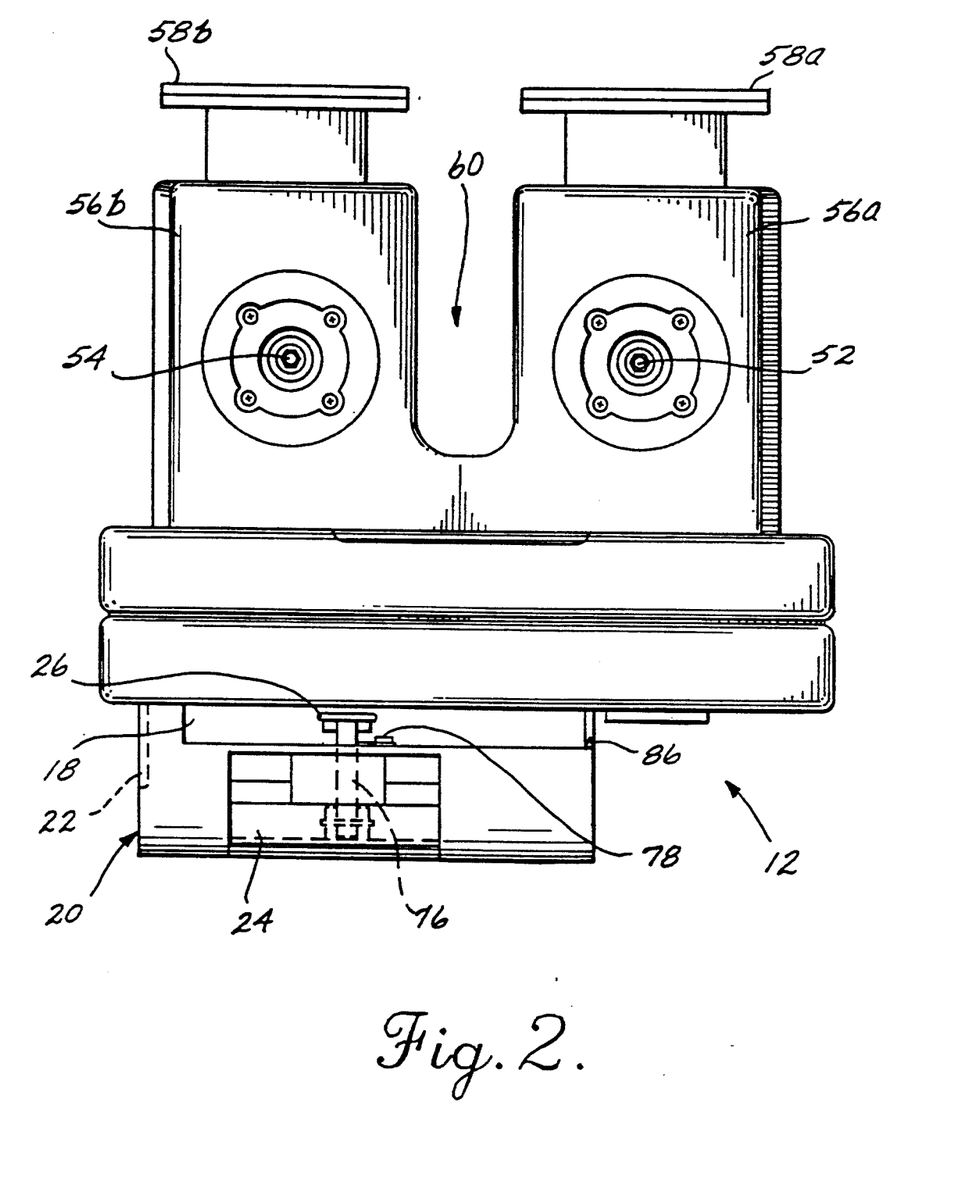
FIG. 2 is a top view of the calibrator.
Figure 3:
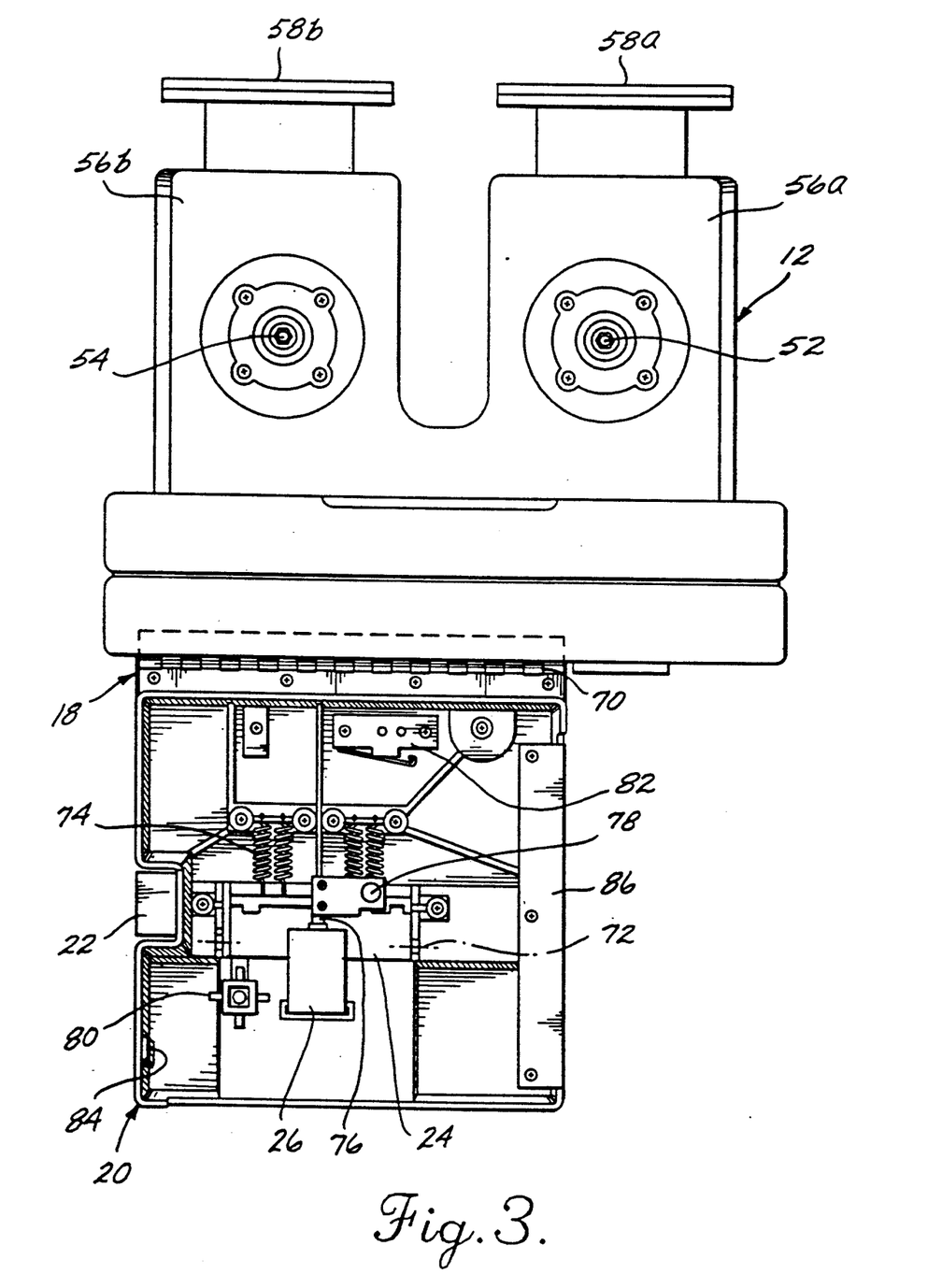
FIG. 3 is a view of the door of the calibrator, of the side of the door that contacts the tray.
Figure 10:
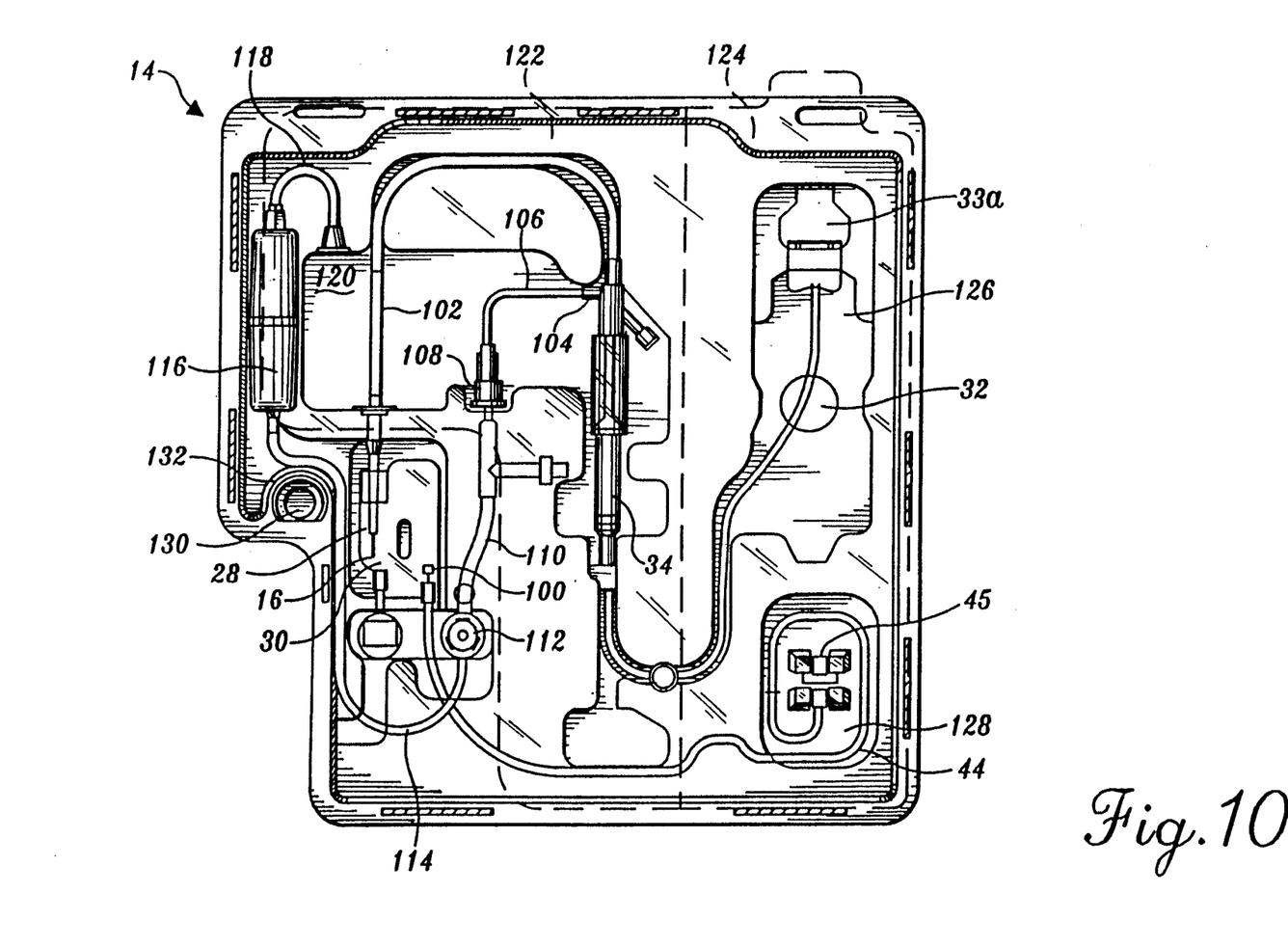
FIG. 10 is a plan view of the tray showing the medical sensor as it is stored prior to use and during calibration.

It will be necessary to refer to each of FIGS. 1 through 5 and 10 from time to time throughout this Description, to fully understand and appreciate all of the features of the present invention. A calibration system 10 is shown in FIG. 1 for use in calibrating a medical sensor 16, which is shown in FIG. 10. Calibration system 10 includes a calibrator 12 that is illustrated in whole or in part in FIGS. 1 through 5. Calibrator 12 is used in connection with a display unit 36 and a tray 14, portions of which are shown in FIGS. 1 and 3. Medical sensor 16 is calibrated while it remains in tray 14, a housing in which the medical sensor 16 is maintained in a sterile environment, both before and during its calibration, and certain aspects of tray 14 are critical to the operation of calibration system 10. Accordingly, details of the tray are shown in FIG. 10, and a more detailed description of tray 14 is provided in U.S. Pat. No. 5,011,836. Since the disclosure of that patent is incorporated herein by reference, it is not necessary to repeat the complete description of the tray and its configuration; however, reference will be made to FIG. 10 in describing how calibrator 12 is used in connection with tray 14.

During its calibration, the medical sensor housed within tray 14 is positioned vertically within a slot 18 defined between a hinged panel 20 and the remainder of calibrator 12. As shown in FIG. 1, hinged panel 20 is latched in place in a vertical or upright position to hold tray 14 during the calibration process. A latch 22 (not visible in FIG. 1), disposed on the left edge of panel 20 is released to swing the top of panel 20 downwardly in order to expose the interior of the panel. Panel 20 also includes a heater planten release handle 24, which is pivoted outwardly to disengage a heater platen 25 (FIG. 5) from its point of contact with a tonometry chamber 28 (FIGS. 4 and 5) that is defined in tray 14. Tonometry chamber 28 encloses medical sensor 16, which in the preferred embodiment, comprises a blood gas sensor capable of sensing the pH, $pCO_2$, $pO_2$, and temperature of a liquid (such as blood) in which the medical sensor is immersed. Medical sensor 16 is shipped and stored in tray 14, immersed in a liquid 30 within tonometry chamber 28. Prior to calibration, this liquid maintains the medical sensor in a hydrated state. The liquid is injected into tonometry chamber 28 when the medical sensor is packaged within tray 14, prior to shipment to an end user.

Referring to FIG. 1, calibrator 12 is coupled to display unit 36 through a control line 42. Display unit 36 includes a display screen 38 in which data indicative of the chemical parameters sensed by medical sensor 16 are displayed, along with other textual information and data. A plurality of control buttons 40 are provided on the display unit 36 to control operation of the medical sensor and display unit during the actual use of the device. In addition, prior to its use, medical sensor 16 is calibrated using the calibration procedure described below, which is initiated by the operator's selection of one of the control buttons on display unit 36 that is labeled "CALIBRATE."

Display unit 36 communicates bi-directionally with calibrator 12 through control line 42, receiving signals indicative of ambient barometric pressure and monitoring status of the calibrator 12. As shown in FIG. 10, medical sensor 16 is disposed at the distal end of a sensor line 32, and a connector 33 is disposed on the opposite end of the sensor line, which, as shown in FIG. 1, is joined to an extension line 35 during the calibration. Sensor line 32 and extension line 35 comprise optical fibers that convey a light signal indicative of the blood gas chemical parameters sensed by medical sensor 16 and conductive leads that convey an electrical signal indicative of the temperature at the distal end of the medical sensor; however, the optical fibers and conductive leads are not separately shown. The extension line carries the signals from the medical sensor to the display unit, which processes the data to determine the blood gas levels. Sensor line 32 passes through a delivery device 34 that remains inside tray 14; the delivery device is used to insert the medical sensor into the vascular system of a patient and is disclosed in commonly assigned U.S. Pat. No. 5,112,309.

A tube 44 extends from tray 14 in FIG. 1 and is connected to a gas port 46 on panel 20, through a Luer fitting 45 that is disposed on the distal end of the tube. Tube 44 provides fluid communication with internal plumbing lines (not illustrated) in calibrator 12, receiving a first calibration gas from a storage bottle 48. The first calibration gas is carrid by tube 44 into tonometry chamber 28 and is bubbled through liquid 30, saturating it. While the first calibration gas is bubbling through liquid 30, the liquid is heated to a calibration temperature with heat applied from heater platen 26. The first calibration gas saturates the liquid with carbon dioxide and oxygen, achieving known partial pressures of $CO_2$ and $O_2$, determined based upon the chemical composition of the first calibration gas, the temperature of the liquid, and the ambient barometric pressure. This saturated condition of liquid 30 represents a first calibration point at which medical sensor 16 is calibrated. Thereafter, a second calibration gas from gas storage bottle 50 is conveyed through tube 44 into tonometry chamber 28, bubbling through liquid 30 until a second calibration point is achieved. The second calibration point again represents partial pressures for $CO_2$ and $O_2$ that are determined based upon saturation of the liquid by a known chemical composition of the second calibration gas, the calibration temperature of the liquid, and the observed ambient barometric pressure.

FIG. 2 illustrates rear chassis portions 56a and 56b of calibrator 12, which contain a calibration gas bottle connector port 52 for the first calibration gas storage bottle and a calibration gas bottle connector port 54 for the second calibration gas storage bottle. Ports 52 and 54 are threaded to receive mating threaded mouths of the corresponding calibration gas storage bottles. In the preferred embodiment, the first calibration gas comprises 8.3% $CO_2$, 8.3% $O_2$, and the remainder is $N_2$. Similarly, the second calibration gas comprises 2.8% $CO_2$, 21% $O_2$, and a balance of $N_2$. While the preferred embodiment uses two calibration gases, it will be apparent to those of ordinary skill in the art that additional calibration points can be obtained by replacing the first and second calibration gas storage bottles with third and fourth calibration gas storage bottles containing third and fourth calibration gases having different compositions than the first and second calibration gases. It may also be possible to calibrate at a single calibration point, requiring only one of the calibration gases to be bubbled through liquid 30 until a saturation of the liquid with the gas occurs.

In addition to containing the ports for connection with the calibration gas storage bottles, rear portions 56a and 56b includes pedestals 58a and 58b on which the communication cable and a power input cord (not shown) can be stored when not in use. Between rear portions 56a and 56b, a post slot 60 is defined, sufficiently deep so that the center of gravity of calibrator 12 is approximately coincident with the center end portion of the slot, enabling stable support of the calibrator by a medical instrument stand (or post—not shown), which might also be employed for supporting the display unit.

Above gas port 46 on panel 20 is disclosed a two-color, light emitting diode (LED) 62 (FIG. 1), which flashes yellow if the pressure of gas in either of the first or second calibration gas storage bottles is either insufficient to begin a calibrator or is sufficient only to complete the current calibration. If the gas pressure level is above the minimum required, the LED emits a green light.

Figure 4:
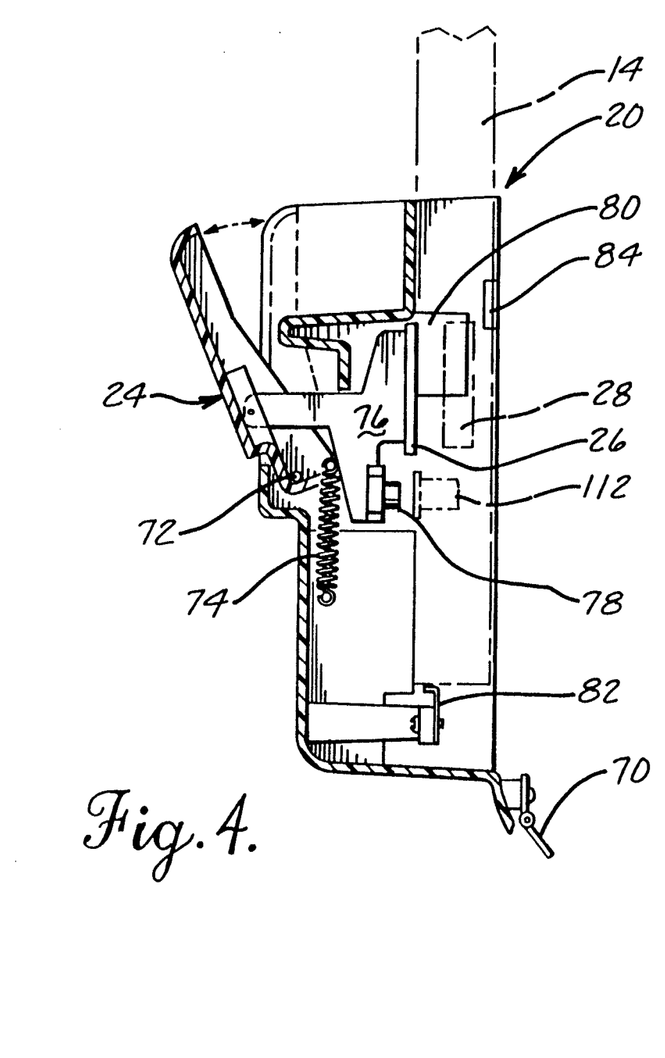
FIG. 4 is a sectional side view of the calibrator, showing a heater disengaged from the tray, as required for insertion or removal of the tray.
Figure 5:
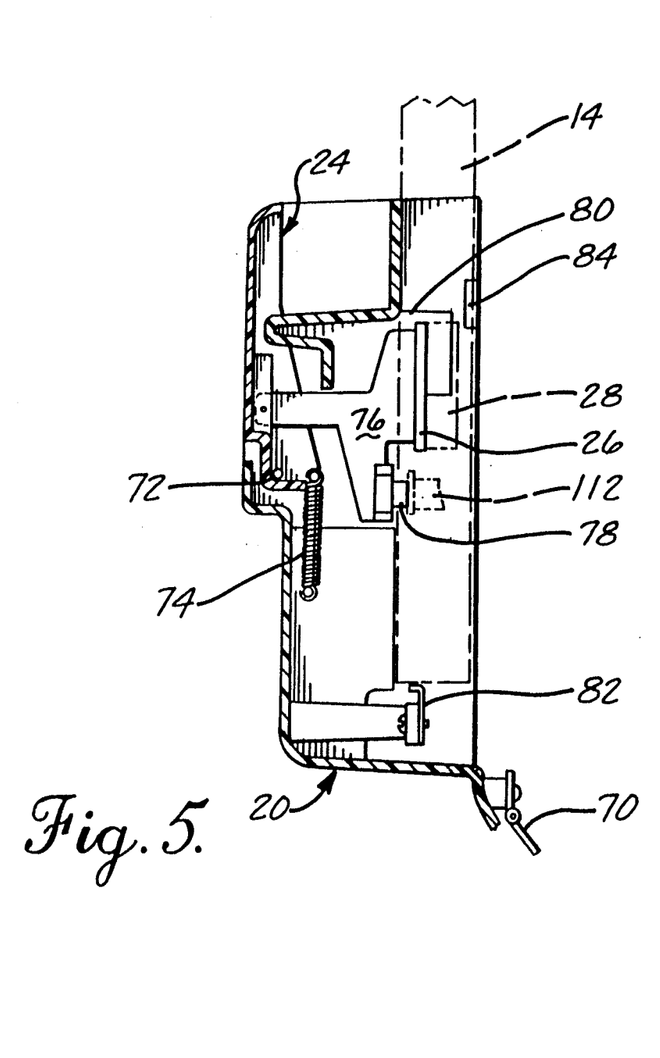
FIG. 5 is a sectional side view of the calibrator, showing the heater positioned to heat a portion of the tray containing the medical sensor.

With reference to FIGS. 4 and 5, a hinge 70 is illustrated along the bottom edge of panel 20, providing a pivotal connection about which panel 20 rotates downwardly away from the remaining portion of the calibrator. Also shown is a release handle hinge 72 that pivotally connects handle 24 along its lower edge. Release handle 24 is biased inwardly about release handle hinge 72 by four helical springs 74 that extend vertically between the interior of panel 20 and the lower inside edge of release handle 24. Release handle 24 is pivotally connected to a heater support plate 76, which extends inwardly of panel 20, toward the rear of calibrator 12. Heater platen 26 is transversely connected to the inwardly extending edge of heater support plate 76 and comprises a generally rectangular metal plate having a rear surface along which a heating element (not separately shown) is bonded. The heater platen is sized to overlie the tonometry chamber formed within tray 14. When tray 14 is positioned in slot 18 and assuming that an operator is not holding release handle 24 and heater platen 26 away from tray 14, helical springs 74 apply a biasing force that acts to bring the heater platen into thermal contact with a surface of the tonometry chamber so that heat can efficiently transfer between the heater platen and liquid 30 within the tonometry chamber. The pivotal connection of heater support plate 76 to release handle 24 ensures that heater platen 26 will align with the surface of the tonometry chamber, even if that surface is not precisely vertical.

Attached to one side of heater support plate 76 is an inwardly extending valve actuator 78. Valve actuator 78 moves with release handle 24 and heater platen 26, under the biasing force of helical springs 74. When tray 14 is in place in slot 18 for calibration of medical sensor 16, the biasing force of the helical springs causes valve actuator 78 to depress, i.e., open a normally closed valve 112 (shown in FIG. 10), enabling gas to flow through tonometry chamber 28, as will be explained below. To insert tray 14 within slot 18 of calibrator 12, an operator grasps the top portion of release handle 24, pivoting it outwardly so that the heater platen and valve actuator 78 clear surface of tray 14 as it is inserted vertically into calibrator 12. Thereafter, release handle 24 is allowed to pivot inwardly under the urging of helical springs 74, bringing heater platen 26 into contact with the tonometry chamber and opening valve 112 with valve actuator 78. To assist in properly positioning tray 14 within slot 18 and to ensure that heater platen 26 aligns with the surface of tonometry chamber 28, a positional reference post 80 is formed on the inside of panel 20, extending rearwardly into slot 18. The positional reference post engages a corresponding tray reference feature 132 (FIG. 10) on tray 14, orienting the tray within slot 18 in the required position for calibration of the medical sensor. A tray sensor switch 82 is disposed along the lower edge of slot 18 and comprises a micro switch that responds to the operator's positioning of tray 14 in calibrator 12 for calibration of the medical sensor.

Since heater platen 26 reaches temperatures that might risk burning the fingers of personnel touching the heater platen when panel 20 is open, a magnet 84 is mounted to the inside edge of panel 20 and serves to actuate a magnetic reed switch (not shown) when the panel is closed and latched.

Running substantially along the entire right hand inner edge of panel 20 is a tear bar 86 (FIG. 1), which is sharp or serrated to facilitate tearing part of a TYVEK ™ membrane 124 from a remaining portion 122. It will be apparent that portion 124 of the membrane covers both a chamber 126 in which a connector 33a is disposed and a chamber 128 in which the distal end of tube 44 is disposed. Removal of membrane 124 exposes connector 33a on the distal end of sensor line 32, and both Luer fitting 45 and the proximal end of tube 44. These portions of the apparatus in tray 14 must be accessible to carry out the calibration of the medical sensor. The remaining portion 122 of the TYVEK ™ membrane that is not torn away continues to cover and protect the sterility of portions of the apparatus associated with the medical sensor that would otherwise be exposed, including delivery device 34, until after the calibration is completed. The sterile environment in which the medical sensor and its associated apparatus have been stored is thus maintained, since portion 122 of the TYVEK ™ membrane prevents the medical sensor and its apparatus from being exposed to bacteria, while allowing the first and second calibration gases to pass through the membrane. In FIG. 10, the TYVEK ™ membrane is shown outlined with dash lines.

Calibration gas flowing through tube 44 enters tonometry chamber 28 through an orifice 100 as a stream of bubbles. Since the tonometry chamber is approximately two-thirds full of liquid 30, the stream of bubbles circulates through the liquid, stirring it to achieve a uniform or homogenous saturation of the liquid with $CO_2$ and $O_2$. After bubbling through the liquid, the first or second calibration gas passes into tubing 102. It is important for tray 14 to be substantially vertically oriented during the calibration procedure to ensure that medical sensor 16 is maintained immersed in liquid 30 and to enable the first or second calibration gas to flow into tubing 102 after it bubbles through the liquid. Tubing 102 is connected to delivery device 34, and the first or second calibration gas passes through a side port 104 on the delivery device and into tubing 106. The end of tubing 106 is connected to a bulkhead fitting 108, the other side of which is coupled to tubing 110 that conveys the first or second calibration gas to normally closed valve 112. However, during the calibration, as explained above, valve actuator 78 opens normally closed valve 112, enabling the flow of the calibration gases therethrough. The first or second calibration gas is then conveyed through tubing 114 to a moisture filter 116, which removes any residual liquid 30 entrained in the gas. First or second calibration gas exiting moisture filter 116 is conveyed through tubing 118 into a chamber 120. The gas entering chamber 120 passes through portion 122 of the TYVEK ™ membrane covering the chamber and into the surrounding ambient atmosphere.

Tray reference feature 132, formed as a notch in the tray in the preferred embodiment, accommodates positional reference post 80 and also serves to align an optional electrical contact (not separately shown in the figures) formed on the end of positional reference post 80 with a memory token 130. Memory token 130 is an optional feature disposed in tray 14 and can electronically store data, such as the expiration date for the medical sensor, preliminary calibration data determined at the time that the medical sensor is manufactured, or other information related to the use and/or calibration of the medical sensor. Memory token 130 comprises an electronic memory device having two opposed surfaces that define electrical contacts through which data can be read or written in a serial data signal. One side of memory token 130 is contacted by positional reference post 80, and the opposite surface is contacted by an optional electrical conductor (not separately shown) that is disposed on the opposite side of slot 18 when tray 14 is properly positioned within calibrator 12 for calibration of the medical device. Data stored in the memory token can be read, or data can be stored in the memory token through signals passed via the electrical contacts thereby made the opposed surfaces of the memory token.

Figure 6:
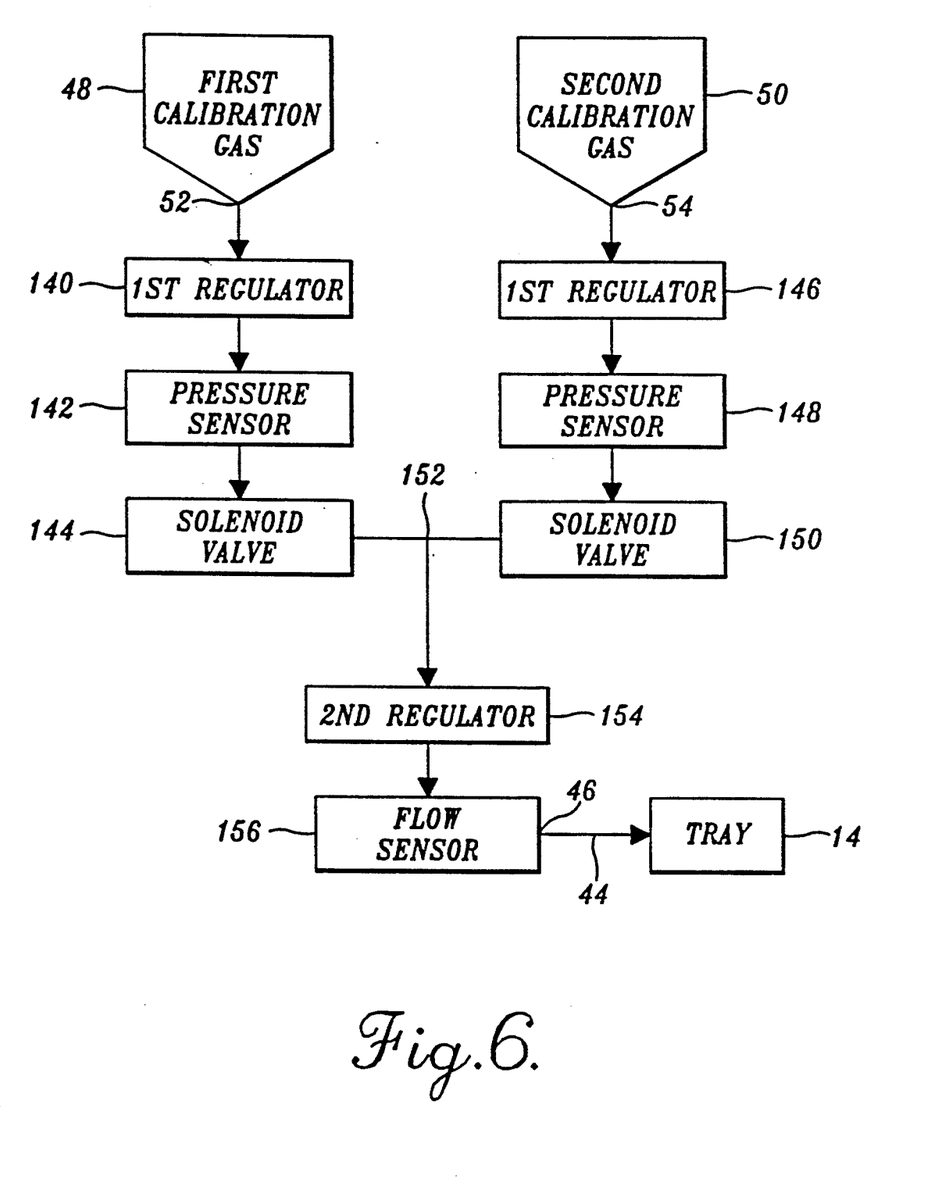
FIG. 6 is a block diagram of a calibration gas supply system in the calibrator.

FIG. 6 illustrates a block diagram for the first and second calibration gas system flow paths. As illustrated therein, first calibration gas storage bottle 48 is coupled through port 52 to a first regulator 140 that reduces the pressure within the gas storage bottle to approximately 45 psig. First regulator 140 is active so long as the pressure of the first calibration gas is greater than 45 psig. Once the pressure in the first calibration gas storage bottle falls below that level, first regulator 140 simply allows the first calibration gas to flow from first calibration gas storage bottle 48 without any significant effect on its pressure. A pressure sensor 142 monitors the output pressure of first regulator 140, and produces a signal indicative of the gauge pressure at that point, for use in determining if the pressure is adequate to complete a calibration. A solenoid valve 144 controls the flow of first calibration gas from first regulator 140, through pressure sensor 142, into a common tee line 152.

Second calibration gas storage bottle 50 is similarly coupled through port 54 to a first regulator 146, which likewise reduces the pressure of the second calibration gas to approximately 45 psig. A pressure sensor 148 monitors the pressure of the second calibration gas to determine if sufficient gas pressure is available to complete a calibration. Downstream of pressure sensor 148, a solenoid valve 150 controls the flow of the second calibration gas into common tee line 152. The common tee line is connected to the input of a second regulator 154, which further reduces the pressure of either the first or second calibration gas (as determined by whichever of solenoid valves 144 or 150 has been opened, since only one of the solenoid valves is opened at a time). The output pressure from second regulator 154 is approximately 10–11 psig. A flow sensor 156 determines if either the first or second calibration gas is flowing through gas port 46 into tubing 44 and in a preferred embodiment, comprises a sapphire orifice and differential pressure sensor (neither separately shown). Flow sensor 156 thus produces a signal indicative of gas flow through gas port 46, which is used as explained below. As already noted, tube 44 conveys either the first or the second calibration gas selected by actuation of solenoid valves 144 or 150, into the tonometry chamber within tray 14.

Figure 7:
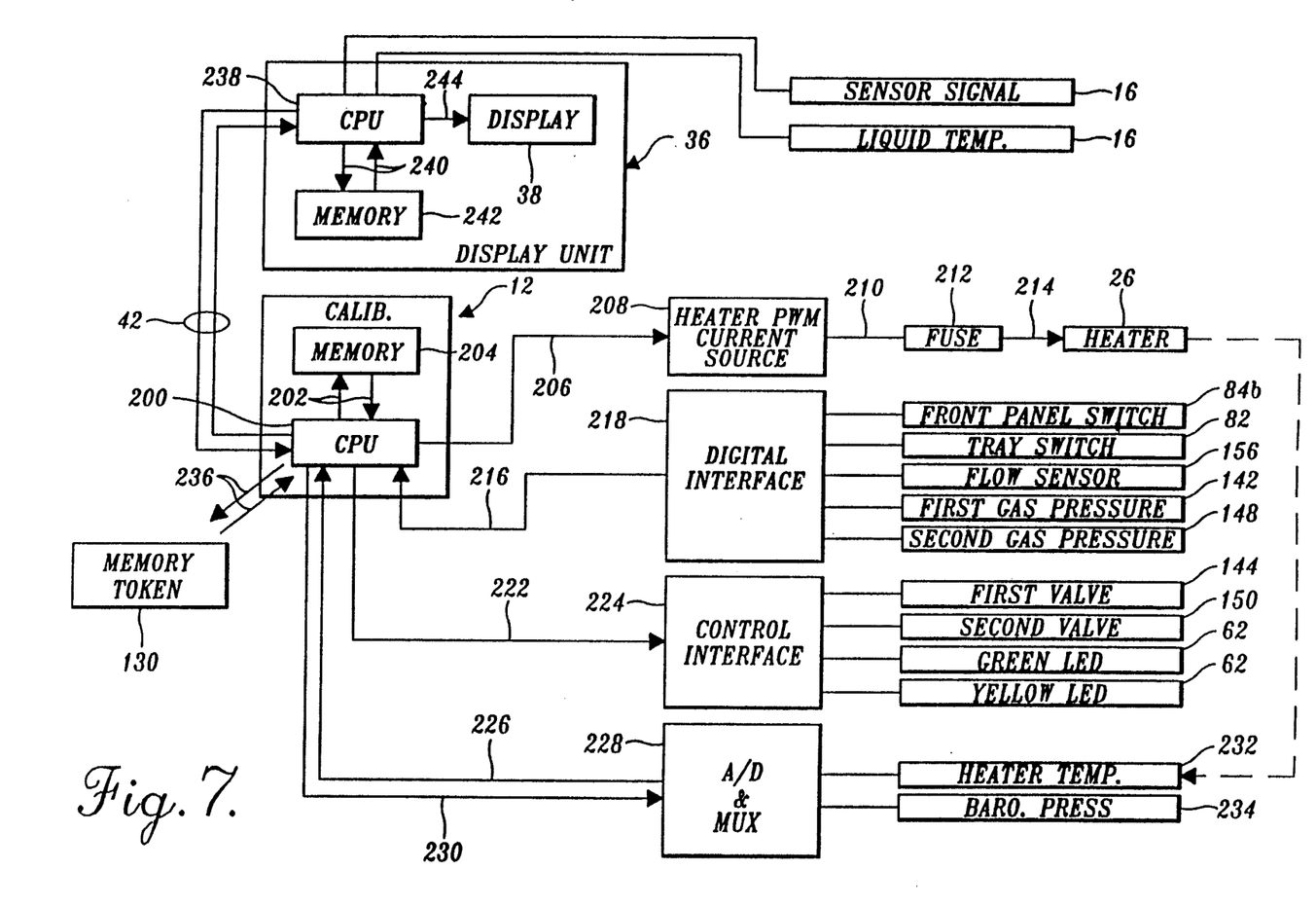
FIG. 7 is a block diagram of an electrical system in the calibrator and associated display unit.

FIG. 7 illustrates the components of the electrical system in the calibration system. Calibrator 12 includes a CPU 200, which in the preferred embodiment comprises an INTEL ™ type 8051 microprocessor. CPU 200 is connected by address/data lines 202 to a memory circuit 204, comprising read only memory (ROM), random access memory (RAM), and electrically erasable programmable read only memory (EEPROM). Memory circuit 204 stores instructions necessary for CPU 200 to carryout the calibration procedure and in addition, stores instrument specific parameters that are used during the calibration process. A line 206 connects CPU 200 to a heater pulse width modulated (PWM) current source 208, allowing the CPU to control the operation of the current source that supplies PWM current to heater platen 26, and thus the power provided to heat the liquid in the tonometry chamber. A line 210 conveys the PWM current through a thermal fuse 212 (embedded in heater platen 26) and a line 214 couples the PWM current to heater platen 26. Thermal fuse 212 opens, interrupting current flow if the temperature of the heater platen exceeds a predefined maximum, which should not happens unless a malfunction has occurred.

The temperature of heater platen 26 is rapidly increased to achieve a temperature in liquid 30, which closely approximates the expected temperature (e.g., 37° C.) at which medical sensor 16 will be used during monitoring of the chemical blood gases in the vascular system of a patient. The algorithm used to control the temperature of heater platen 26 and thus the temperature of liquid 30 during the calibration is explained in detail below.

Digital signals are conveyed to CPU 200 over lines 216 from a digital interface 218. The digital signals are the following: the output of a reed switch represented by a block 84b, which is activated by magnet 84 on the lip of panel 20, the signal from tray sensor switch 82, the signal from flow sensor 156, the signal indicative of a first calibration gas pressure from pressure sensor 142, and the signal indicative of the second calibration gas pressure from sensor 148.

Lines 222 convey control signals from CPU 200 to a control interface circuit 224 that provides the appropriate control signal to actuate one of: first solenoid valve 144, second solenoid valve 150, and LED 62 (either green light, or the yellow blinking light).

Lines 226 convey digital signals from a combination analog-to-digital converter (ADC) and multiplexer (MUX) 228, following conversion of the signals from analog to digital format. The specific signal selected is in response to a control signal from CPU 200 conveyed over a line 230. The analog signals available for selection include: a heater-temperature signal produced by a heater-temperature sensor 232 (embedded in heater platen 26) and an ambient barometric pressure signal produced by a barometric pressure sensor 234. In response to the signal from CPU 200, combination ADC and MUX 228 selects one of these two analog signals, converts it to digital formal, and conveys it over line 226 to CPU 200. Lines 236 are optionally coupled to memory token 130 when tray 14 is positioned in place for calibration of medical sensor 16, as already described above. If memory token 130 is used, CPU 200 can read and/or write data from or to the memory token.

The calibration of medical sensor 16 is initiated in response to a signal supplied from display unit 36 over control lines 42. Display unit 36 inlcudes a CPU 238, which in the preferred embodiment comprises an INTEL ™ type 80286 microprocessor. CPU 238 is coupled through address/data lines 240 to a memory circuit 242, which includes both ROM and RAM. In addition, a line 244 couples CPU 238 to display 38. CPU 238 receives the signals produced by medical sensor 16 that are indicative of chemical parameters to which the medical sensor is responsive, and the temperature of liquid 30 as indicated by a signal produced by a thermistor (not separately shown) comprising medical sensor 16. During the calibration process, liquid 30 becomes saturated with the first and second calibration gases, yielding two calibration points for each of the three different chemical blood gas parameters to which the medical sensor is sensitive. The temperature at which the calibration is carried out is determined by the temperature sensor comprising medical sensor 16. CPU 238 determines the measured values for the chemical parameters using the signal output by the medical sensor at the first and second calibration points. By correlating the values thus determined against expected values, CPU 238 determines calibration coefficients that subsequently are applied to the measurements by medical sensor 16 when it is used for monitoring chemical blood gases in a patient. So long as medical sensor 16 remains coupled to display unit 36, the calibration coefficients thus determined are retained for use with the medical sensor.

Figure 8:
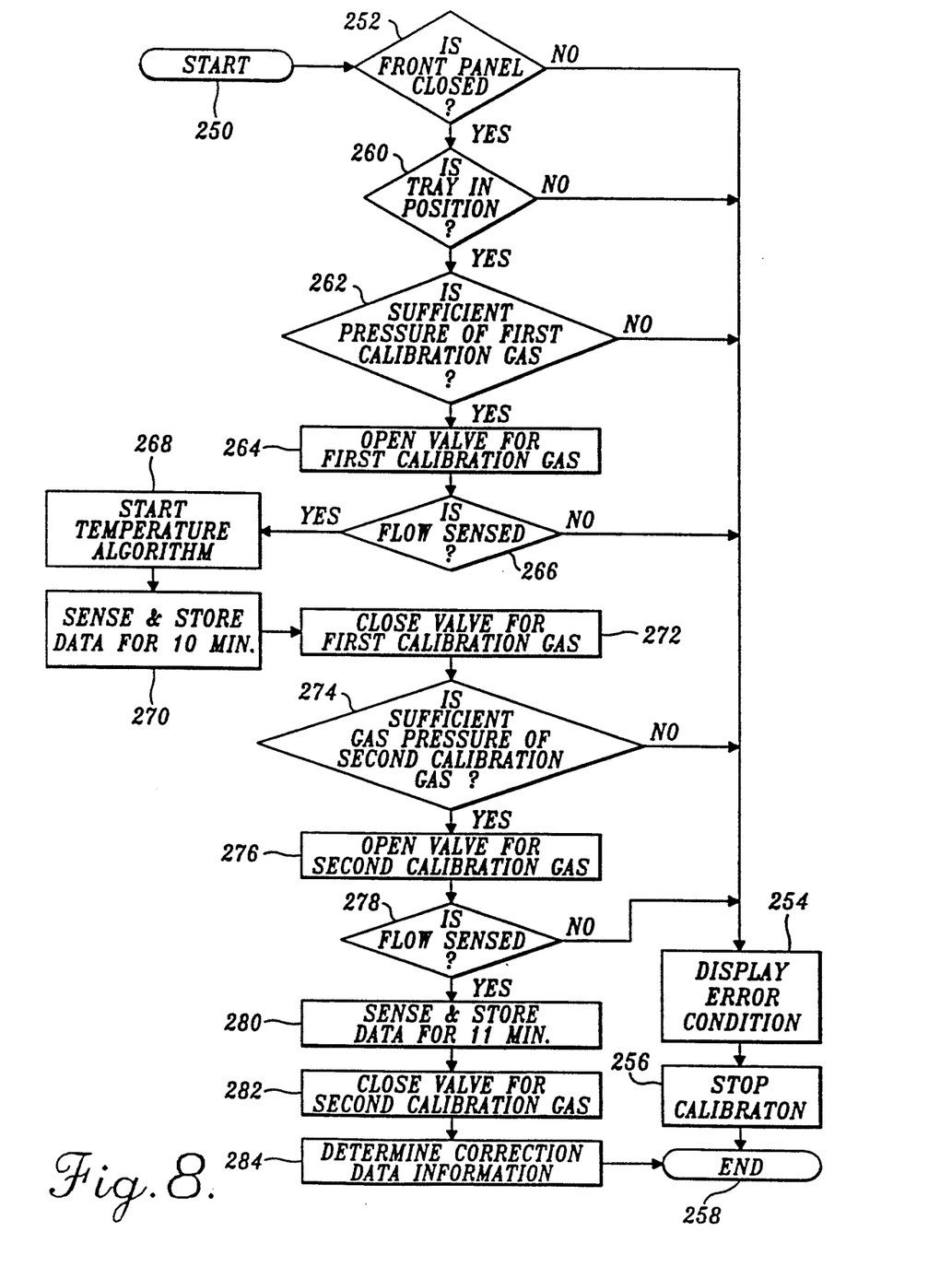
FIG. 8 is a flow chart showing the overall logic implemented in the calibration process.

The steps of the calibration process are shown in a flow chart in FIG. 8. After a start block 250, a decision block 252 determines if panel 20 is closed and latched. If not, the control proceeds to a block 254 wherein display unit 36 indicates an error condition. Thereafter, a block 256 stops the calibration process, and the logic proceeds to an end block 258. However, if the front panel is closed, the logic proceeds to a decision block 260, which determines if tray 14 is positioned properly in slot 18. If not, block 254 indicates an error has occurred that again results in termination of the calibration. Assuming that the tray is properly positioned, the logic proceeds to a decision block 262 to determine if sufficient pressure is available in the first calibration gas storage bottle to complete the calibration, e.g., a pressure in excess of 45 psig. If not, the calibration process is terminated, as already explained above, with reference to block 254. If the gas pressure is adequate to proceed, a block 264 opens solenoid valve 144, allowing the first calibration gas to flow into second regulator 154. Thereafter, a decision block 266 determines whether flow sensor 156 has detected flow of the first calibration gas through gas port 46. If not, the calibration is terminated as explained above. When flow through the output port of calibrator 12 is detected, a block 268 starts a temperature algorithm, which is explained below with reference to FIG. 9A and 9B.

Display unit 36 then begins to receive data resulting from the output of medical sensor 16 for approximately 11 minutes, as indicated in a block 270. The data produced from near the end of that 11-minute interval will be used to determine the first calibration point as a function of the calibration values, which are based upon the ambient barometric pressure, at the calibration temperature determined by the medical sensor, and the calibration gas composition. A block 272 then closes solenoid valve 144, terminating the flow of the first calibration gas.

A decision block 274 checks to determine if there is sufficient gas pressure of the second calibration gas to complete the calibration, and if not, the logic proceeds to blocks 254 and 256. However, assuming that there is adequate pressure, a block 276 opens solenoid valve 150, allowing the second calibration gas to flow. A decision block 278 determines if gas flow is sensed by flow sensor 156 and if not, the calibration is again terminated. Otherwise, CPU 238 begins taking data for the next 11 minutes, the data stored during the end of this period being subsequently used to determine the correction factors for each of the chemical blood gases monitored by medical sensor 16. After this interval has elapsed, a block 282 closes solenoid valve 150, terminating the flow of the second calibration gas. Finally, in a block 284, the calibration coefficients to be applied are determined by CPU 238 and stored for use with medical sensor 16. End block 258 finishes the procedure.

A further aspect of this invention relates to the algorithm by which the heater platen attains the desired calibration temperature, which is 37° C. in the preferred embodiment, and maintains it during the calibration process. Since it may be important to complete a calibration as rapidly as possible to enable to a medical sensor to be used with a patient in an emergency, it is important that the calibration temperature be achieved as quickly as posible. Further, the calibration temperature must be held constant at the desired level to within approximately ±0.5° C. during the calibration process. The algorithm used to control the temperature of heater platen 26 is illustrated in the flow chart in FIGS. 9A and 9B. From a start block 290, a block 292 provides the heater with full power, i.e., heater PWM current source 208 supplies a constant maximum rated current to the heater platen to rapidly increase its temperature. In a block 294, the control extrapolates the temperature of liquid 30 over a predefined time interval into the future, which in the preferred embodiment, is 15 seconds. A decision block 296 determines if the extrapolated temperature is greater than or equal to a target temperature, e.g., the desired calibration temperature at which the medical sensor will be used. If not, step 294 is repeated until the condition in decision block 296 is satisfied. Thereafter, a block 298 sets the heater power to a zero current. Then, a block 300 causes the control to wait until the temperature of liquid 30 begins to decrease. Once the decrease is detected by medical sensor 16, a decision block 302 determines if the liquid temperature is less than a minimum predefined temperature. In the preferred embodiment, the minimum predefined temperature is 36° C. If so, a block 304 sets a target temperature to the predefined minimum temperature and proceeds to a decision block 306.

Figure 9A:
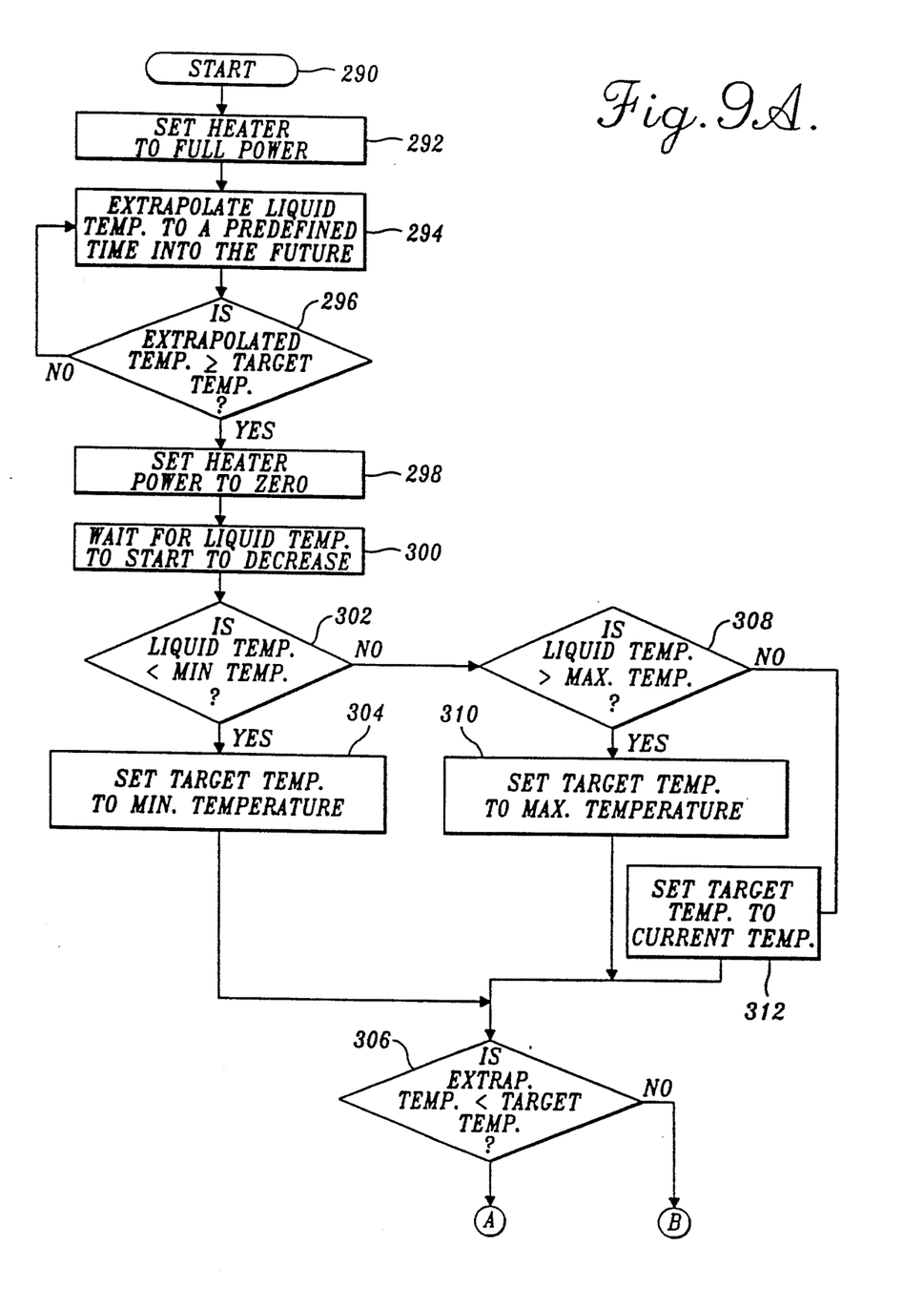
FIGS. 9A and 9B illustrate a flow chart showing the logic for controlling the temperature of a liquid in which the medical sensor is immersed, to achieve a desired calibration temperature.
Figure 9B:
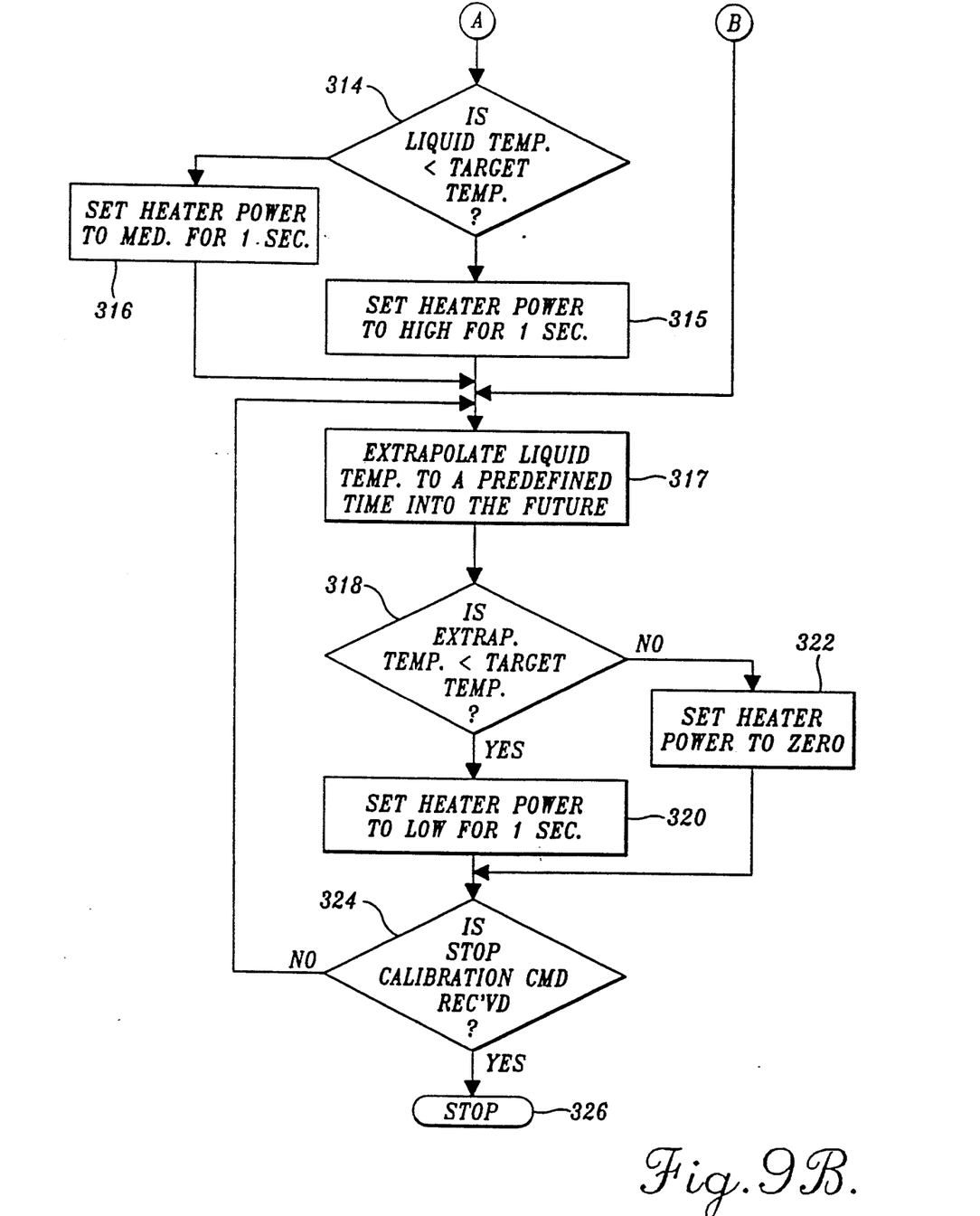

If the response to decision block 302 is negative, a decision block 308 determines if the liquid temperature is greater than a predefined maximum temperature (38° C. is the predefined maximum temperature in the preferred embodiment). If so, a block 310 sets the target temperature to the predefined maximum temperature. Otherwise, the target temperature is set to the current temperature of the liquid in a block 312.

The logic then proceeds to decision block 306, to determine if the extrapolated temperature is less than the target temperature. If it is, then a further inquiry is made to determine if the liquid temperature is less than the minimum temperature in decision block 314. If the result of this determination is negative, a block 316 causes the heater PWM current source to provide a medium power level to heater platen 26 for one second. Otherwise, the a high power level is provided to heater platen 26 for one second, as indicated in a block 315. The logic then continues with a block 317.

Assuming that a negative response to decision block 306 is obtained, the logic proceeds to block 317, leaving the heater power still set to zero current level. Block 317 extrapolates the liquid temperature over a predefined time interval into the future, which again, is 30 seconds in the preferred embodiment. After block 317, a decision block 318 determines if the extrapolated temperature is less than the target temperature, and if not, sets the heater power to zero in a block 322. Thereafter, a decision block 324 determines if the stop calibration command has been received (issued in block 256 in FIG. 8) and if so, stops the application of power to the heater platen in a block 326. If not, the logic loops back to block 317, where the extrapolation of the temperature is repeated, and decision block 318 re-entered. If the response to decision block 318 is affirmative, a block 320 sets the heater power to a predefined low level for one second and proceeds to decision block 324. Blocks 318 through 324 thus provide for maintenance of the temperature of heater platen 26 at the target temperature, which is the calibration temperature ±0.5° C. in the preferred embodiment. This process continues during saturation of liquid 30 with the first calibration gas, followed by saturation with the second calibration gas, until the stop calibration command is issued or the calibration is completed.

While the present invention has been disclosed in connection with a preferred embodiment and modifications thereto, those of ordinary skill in the art will appreciate that other changes can be made within the scope of the claims. Accordingly, the scope of the invention is to be determined entirely by reference to the claims that follow and is not in any way limited by the disclosure.

The embodiments of the invention in which an exclusive property or privilege is claimed are defined as follows:

1. A calibration system for calibrating a medical sensor sensitive to a chemical parameter, said medical sensor being disposed in a liquid pool contained within a housing that maintains the medical sensor in a sterile environment during calibration of the medical sensor prior to its in vivo use, said calibration system comprising:

(a) a chassis adapted for supporting a housing in which a medical sensor is disposed and maintained in a sterile condition during calibration of the medical sensor;

(b) a heater disposed on the chassis, said heater being adapted for heating a liquid in a portion of the housing in which the medical sensor is disposed, to a predefined calibration temperature;

(c) a source of a first calibration gas connected in fluid communication with a connector, said connector being adapted to connect to a fluid line that extends from the housing to enable the first calibration gas to bubble through the liquid in which the medical sensor is disposed;

(d) valve means, connected in fluid communication with and between the source of the first calibration gas and the connector, said valve means being opened to enable a flow of the first calibration gas through the connector during the calibration of the medical sensor, said valve means controlling the flow of the first calibration gas through the liquid to achieve a first predefined chemical calibration point in the liquid;

(e) biasing means, disposed on the chassis, for biasing the heater against the housing to ensure heat transfer from the heater to the liquid in which the medical sensor is disposed; and (f) temperature control means, electrically coupled to the heater, said temperature control means being adapted to connect to a lead coupled to the medical sensor that conveys a signal produced by the medical sensor, which is indicative of the temperature of the liquid, said temperature control means controlling the temperature of the heater so that the liquid in which the medical sensor is disposed is heated to the predefined calibration temperature and maintained at the predefined calibration temperature during the calibration of the medical sensor.

2. The calibration system of claim 1, wherein the heater comprises a metallic plate and a resistive heating element coupled to the metallic plate, said biasing means providing a force that brings the metallic plate into contact with a surface of the housing adjacent a chamber in which the medical sensor is disposed in the liquid to effect heat transfer through the surface into the liquid within the chamber.

3. The calibration system of claim 1, further comprising a source of a second calibration gas that is different than the first calibration gas, said valve means selectively coupling the source of the second calibration gas in fluid communication with the connector to enable the second calibration gas to bubble through the liquid in which the medical sensor is disposed in order to equilibrate the liquid to a second chemical calibration point.

4. The calibration system of claim 3, further comprising pressure regulating means, coupled in fluid communication with the port, for regulating the pressure of the first and the second calibration gases selected by the valve means to flow through the port.

5. The calibration system of claim 1, wherein the chassis includes an alignment projection that is disposed on the chassis in a predetermined position relative to the heater, said alignment projection being thus adapted to engage a corresponding notch on the housing to ensure that the heater overlies a portion of the housing in which the medical sensor is disposed in the liquid.

6. The calibration system of claim 1, further comprising data means for electrically coupling to an electronic memory circuit disposed in the housing, said data means reading data stored in the electronic memory circuit.

7. The calibration system of claim 1, wherein the chassis defines an elongate slot having the heater disposed on one side of the elongate slot, said slot being adapted to receive the housing, said housing comprising a flat, sealed tray that includes a sealed compartment in which the medical sensor is disposed.

8. The calibration system of claim 1, further comprising a pressure regulator, coupled in fluid communication with the connector and the source of the first calibration gas, for regulating the pressure of the first calibration gas flowing through the connector.

9. The calibration system of claim 1, further comprising valve actuator means disposed on the chassis, adapted to engage a normally closed valve disposed in the housing and coupled to the fluid line, for opening the normally closed valve to enable the first calibration gas to flow through the fluid line and into the liquid.

10. The calibration system of claim 1, wherein the biasing means comprise a plurality of springs coupled to the heater, and a lever that when moved, brings the heater into contact with housing, further comprising means for locking the housing in engagement with the chassis when the lever is thus moved.

11. The calibration system of claim 1, further comprising a bar having a tear-edge along at least a portion of one side, said bar being thus adapted to facilitate tearing away part of a sheet-like material that extends over and seals the housing, thereby exposing the fluid line for connection to the connector during the calibration of the medical sensor.

12. The calibration system of claim 1, further comprising a pressure sensor that monitors a pressure of the first calibration gas at the source, said pressure sensor including an indication of said pressure, thus alerting an operator of an insufficient pressure in the source of the first calibration gas, to calibrate the medical sensor.

13. The calibration system of claim 1, further comprising a fluid flow sensor that produces a signal indicative of whether the first calibration gas is flowing through the connector during the calibration of the medical sensor.

14. The calibration system of claim 1, further comprising an over-temperature protective means, disposed on the heater, for disabling the heater if a temperature of the heater exceeds a predefined maximum value.

15. The calibration system of claim 1, further comprising a barometric pressure sensor that produces a signal indicative of ambient barometric pressure for use in correcting the calibration of the medical sensor for barometric pressure effects.

16. The calibration system of claim 1, further comprising switch means for sensing whether the housing is positioned in the chassis and preventing the calibration from proceeding if not.

17. The calibration system of claim 1, further comprising a display for visually displaying the chemical parameter sensed by the medical sensor, said temperature control means comprising a controller in the display means that includes a memory for storing data corresponding to an output signal from the medical sensor at the first predefined chemical calibration point in the liquid.

* * * * *